(12) United States Patent
Clime et al.

(10) Patent No.: US 12,618,104 B2
(45) Date of Patent: May 5, 2026

(54) MICROFLUIDIC CHIP, KIT, AND SYSTEM FOR DISPLACING INDEPENDENT REACTION VOLUMES OF AN EMULSION

(71) Applicant: National Research Council of Canada, Ottawa (CA)

(72) Inventors: Liviu Clime, Longueuil (CA); Lidija Malic, Saint Leonard (CA); Teodor Veres, Montreal (CA)

(73) Assignee: A. National Research Council of Canada, Ottawa (CA)

( * ) Notice: Subject to any disclaimer, the term of this patent is extended or adjusted under 35 U.S.C. 154(b) by 1057 days.

(21) Appl. No.: 17/720,801

(22) Filed: Apr. 14, 2022

(65) Prior Publication Data

US 2022/0333181 A1 Oct. 20, 2022

Related U.S. Application Data

(60) Provisional application No. 63/176,955, filed on Apr. 20, 2021.

(51) Int. Cl.
*C12Q 1/6851* (2018.01)
*B01L 3/00* (2006.01)
(Continued)

(52) U.S. Cl.
CPC .......... *C12Q 1/6851* (2013.01); *B01L 3/5027* (2013.01); *B01L 3/502753* (2013.01);
(Continued)

(58) Field of Classification Search
CPC ............. B01L 3/502753; B01L 3/5027; B01L 3/502784; B01L 7/52; B01L 3/50273;
(Continued)

(56) References Cited

U.S. PATENT DOCUMENTS

| | | | |
|---|---|---|---|
| 10,836,918 B2 | 11/2020 | Malic et al. | |
| 2015/0267246 A1* | 9/2015 | Baroud | ..................... B01L 7/52 |
| | | | 506/37 |
| 2017/0036208 A1* | 2/2017 | Veres | ................ B01L 3/502715 |

FOREIGN PATENT DOCUMENTS

| | | |
|---|---|---|
| WO | 2014056930 A1 | 4/2014 |
| WO | 2015132743 A1 | 9/2015 |
| WO | 2020100039 A1 | 5/2020 |

OTHER PUBLICATIONS

Lidija Malic, Jamal Daoud, Matthias Geissler, Alex Boutin, Ljuboje Lukic, Mojra Janta, Abdelrahman Elmanzalawy and Teodor Veres; Epigenetic subtyping of white blood cells using a thermoplastic elastomer-based microfluific emulsification device for multiplexed, methylation-specific digital droplet PCR, Analyst, 2019, 144,6541-6553.

(Continued)

*Primary Examiner* — Benjamin R Whatley
(74) *Attorney, Agent, or Firm* — Jason E. J. Davis

(57) ABSTRACT

A centrifugal microfluidic technique for heat treating emulsion-divided independent reaction volumes (IRVs) within a centrifugal microfluidic chip, and displacing the emulsion into a monolayer presentation chamber (pc) for imaging. A deep treatment chamber (tc) is provided for the heat treatment, a nozzle having a hydrodynamic radius for forming the IRVs is provided for injecting a sample for the IRVs into the tc filled with a dense immiscible medium. The tc is adjacent a heat controlled element for collectively heat treating the IRVs within the tc, where the IRVs form a 3d packing arrangement. The tc is coupled to a presentation chamber (pc) by an opening through which the IRVs can be selectively displaced without collapsing. The pc is adjacent a window transparent to a wavelength for inspecting the pc.

21 Claims, 4 Drawing Sheets

(51) Int. Cl.
    *B01L 7/00*           (2006.01)
    *B01L 9/00*           (2006.01)

(52) U.S. Cl.
    CPC ........... *B01L 3/502784* (2013.01); *B01L 7/52*
        (2013.01); *B01L 3/50273* (2013.01); *B01L*
        *9/527* (2013.01); *B01L 2200/10* (2013.01);
        *B01L 2200/16* (2013.01); *B01L 2300/0851*
        (2013.01); *B01L 2300/0864* (2013.01); *B01L*
        *2300/1822* (2013.01); *B01L 2400/0409*
        (2013.01); *B01L 2400/0487* (2013.01); *B01L*
        *2400/0694* (2013.01)

(58) Field of Classification Search
    CPC .. B01L 9/527; B01L 2200/10; B01L 2200/16;
        B01L 2300/0851; B01L 2300/0864; B01L
        2300/1822; B01L 2400/0409; B01L
        2400/0487; B01L 2400/0694; B01L
        2200/021; B01L 2400/02; B01L
        2200/0605; B01L 2200/0673; B01L
        2300/0883; B01L 2300/0887; B01L
        2400/0436; B01L 2400/0439; B01L
        2400/086; B01L 3/502715; B01L 7/54;
        B01L 2300/025; B01L 2300/0877; C12Q
        1/6851; C12Q 1/6844; G01N 1/34; G01N
        1/38; G01N 21/75
    See application file for complete search history.

(56)           References Cited

OTHER PUBLICATIONS

Friedrich Schuler, Martin Trotter, Marcel Geltman, Frank Schwemmer, Simon Wadle, Elena Dominguez-Garrido, Maria Lopez, Cristina Cervera-Acedo, Paula Santibanez, Felix Von Stetten, Roland Zengerle and Nils Paust; Digital droplet PCR on disk; Lab on a Chip, Royal Society of Chemistry, Nov. 2015, 16, No. 1; 208-216—Relevant to claims 1-13; p. 209-p. 212, figs 1, 2, 3, 5.

Friedrich Schuler, Clara Siber, Sebastian Hin, Simon Wadle, Nils Paust, Roland Zengerle and Felix Von Stetten; Digital droplet LAMP as a microfluidic app on standard laboratory devices, Analytical Methods, Royal Society of Chemistry 2016, 8 2750-2755.

Bin Li, Yuanming Li, Andreas Manz and Wenming Wu; Miniaturized Continuous-Flow Digital PCR for Clinical-Level Serum Sample Based on the 3D Microfluidics and CMOS Imaging Device, Sensors, 20, 2492; 12 pages.

Fei Hu, Juan Li, Zengming Zhang, Ming Li, Shuhao Zhao, Zhipeng Li and Niancai Peng; Smartphone-Based Droplet Digital LAMP Device with Rapid Nucleic Acid Isolation for Highly Sensitive Point-of-Care Detection; Analytical Chemistry 2020,92; 2258-2265.

J. Madic, A. Zocevic, V. Senlis, E. Fradet, B. Andre, S. Muller, R. Dangla, M. E. Droniou; Three-color crystal digital PCR, Biomolecular Detection and Quantification; 10 (2016) 34-46.

Liviu Clime, Lidija Malic, Jamal Daoud, Luke Lukic, Matthias Geissler and Teodor Veres; Buoyancy-driven step emulsification on pneumatic centrifugal microfluidic platforms; Lab on a Chip, Royal Society of Chemistry, 2020, 20; 3091-3095.

Friedrich Schuler, Frank Schwemmer, Martin Trotter, Simon Wadle, Roland Zengerle, Felix Von Stetten and Nils Paust; Centrifugal step emulsification applied for absolute quantification of nucleic acids by digital droplet RPA; Lap on a Chip Royal Society of Chemistry, 2015, 15, 2759-2766.

Description EP2903738B1 (MT-WO2014056930).

* cited by examiner

MICROFLUIDIC CHIP, KIT, AND SYSTEM FOR DISPLACING INDEPENDENT REACTION VOLUMES OF AN EMULSION

FIELD OF THE INVENTION

The present invention relates in general to treating and handling microfluidic emulsions of regular-sized independent reaction volumes (IRVs), and in particular to a technique for discretizing, processing and presenting in a monolayer, the IRVs without collapsing the IRVs, on a low-cost microfluidic chip.

BACKGROUND OF THE INVENTION

The Covid-19 pandemic has underscored a need for low-cost, available, fast sample to answer systems for genetic testing and quantification, and this, inter alia, is addressed by the present invention.

An emulsion is a useful, elegant and efficient solution to analyzing complex samples. Dividing an already small sample volume into $10^3$-$10^5$ (and potentially $10^6$ or more) isolated, independent reaction volumes (IRVs), allows for simplified reactions with fewer confounding reactions, and a simplified readout process for assessing constituents of the subdivided sample. Isolated by thin webs of an oil or other immiscible fluid, each emulsion-divided IRV can be treated, at the same time, in a same microfluidic chamber.

There are currently several applications leveraging IRVs. For example, nucleic acid amplification assays such as digital droplet PCR (ddPCR), and isothermal digital droplet amplification (e.g. ddLAMP) entail emulsifying PCR or isothermal amplification master mix (which contains primers and probes as well as amplification buffer and appropriate polymerase) as well as sample (i.e. nucleic acid template) which is partitioned into thousands of, for example, nanoliter-scale, IRVs, followed by thermal processing (thermal cycling in the case of ddPCR, or single temperature application in the case of isothermal amplification) and readout (for example, fluorescence or colorimetric).

Unfortunately, the means for forming and manipulating regular sized IRVs are rather technologically involved, requiring expensive, large-footprint, equipment which limits IRV-based technologies. Commercial systems (such as QX 100™ and QX 200™ from Biorad™) or custom research grade devices, can implement complete workflows but typically require manual steps to (1) generate the droplets, (2) transfer the emulsified droplets to PCR tubes in order to perform thermal cycling, and (3) transfer the droplets again from PCR tubes to imaging chambers or droplet readout channels (Malic et al., 2019). These manual steps are laborious and may be prone to pipetting errors which can compromise emulsion integrity and assay repeatability. Furthermore, it must be noted that sample volumes on these (large) scales further limit use of the technologies.

As with all service equipment, there is a trade-off between capabilities to perform a very limited number of protocols, with complete automation, vs. being able to perform a wider number of protocols with limited automation. To provide high levels of automation, the protocol needs to be a sufficiently routine and sufficiently high throughput process to warrant the investment.

For example QX200 ddPCR System™ by BioRAD apparently requires a droplet generator that is 28×36×13 (cm), and a reader that is 66×52×29 (cm), as well as a C1000 Touch Thermal Cycler™ with a particular well reaction module, as well as a PX1 PCR Plate Sealer™. Thus the loading is manual or automated and the well plate needs to be shuffled around between these 4 devices to complete a process.

Sophisticated instruments with embedded robotic systems, such as QX One Droplet Digital PCR System™ from Biorad are capable of automating the entire workflow, however the systems takes significant lab footprint (122× 66×38 (cm)) and costs several hundreds of thousands of dollars. As such, it is beyond the reach of some research laboratories. The system performs sample to answer capabilities on microliter samples.

Another commercial platform, the Naica System™ from Stilla Technologies™, automates emulsification and thermal cycling, however it requires a separate imaging instrument (Madic et al., 2016). The Naica System uses pressurized chambers within a fluid-dynamic network to direct movement of fluids. This requires sophisticated instrumentation and pressure control systems, inducing further complexity in instrument and device design, and adding to costs of equipment and maintenance. There are limited ways that pressure control systems can be integrated into centrifugal microfluidics to achieve similar effect in the state of the art. This system is based on a single prescribed droplet size, which limits customization. Furthermore, the system, like Bio-RAD's, uses 20 ml sample vessels and is essentially macrofluidic.

A few centrifugal microfluidic systems have been developed to integrate droplet generation with thermal processing and post-PCR imaging for ddPCR and ddLAMP assays (Schuler et al., 2016a and 2016b, Li et al., 2020, Hu et al, 2019). Centrifugal microfluidic systems miniaturize assays and reduce reagent consumption and thus the overall cost of the assay, and permit integration of other microfluidic functions to treat the sample prior to emulsification, during treatment, or post imaging; all of which expand the capabilities over closed process lines such as offered by pump-based fluidic systems. Single use centrifugal microfluidic chips can be designed for various processes, integrating smaller volumes of reagents, and offering greater diversity of protocols. Reusable chip controller technologies (referred to herein as a pneumatic, or "P-", blade), such as those claimed by WO 2015/132743, the entire contents of which are incorporated herein by reference, provide addressable pressurized fluid supplies at one or more ports of chips, can further expand processing capabilities of chips while keeping all soiling materials confined to the chip. Centrifugal microfluidic devices are general purpose devices that can be used to provide a very large number of different protocols, depending on the chip structure, loaded contents, and some peripheral devices (e.g. for imaging, and thermal control), unlike special purpose machines that can only perform one protocol.

There are several microfluidic strategies for producing IRVs that have been demonstrated, including several on centrifugal microfluidic chips (Clime et al. 2020, Schuler et al. 2015). While a centrifuge is naturally adapted to forming IRVs, maintaining them during many treatments depends on a fragility of the oil webs separating the IRVs, as well as stresses on the droplets. For example, as stated by Schuler 2016, gas solubility of liquids decreases with rising temperature, and accordingly, the amount of gas released during sample heating to 95° C. can be at least 18 v/v %. Bubbles of gas, in a centrifugal environment, may disrupt oil webs, and merge IRVs.

Automation of a complete protocol, including droplet generation, thermal processing and monolayer generation is still difficult in microfluidic environments. This is mostly due to the difficulty controlling IRV stability during thermal processing and the requirement for IRV monolayer formation for imaging. While this may not be an issue for isothermal amplification at lower temperatures (e.g. 37° C. for RPA, or even possibly 65° C. for LAMP), IRVs, tightly packed into a monolayer (required for droplet imaging), typically cannot withstand thermal processing at elevated temperatures (e.g. 95° C.), such as required for PCR thermal cycling assays without IRV merging, inducing errors in the assay, and decreasing uniformity and efficiency of sampling.

Moreover, most devices described in literature are fabricated using PDMS (a siloxane). While PDMS is often used in academic research, and has good transparency and biocompatibility, the material is incompatible with scaled manufacturing and is rarely used in industry, (e.g. pharmaceutical and clinical research) where biocompatible hard thermoplastics such as polystyrene (PS) and cyclic olefin copolymers (COC) are preferred. PDMS can adsorb proteins and small molecules, biasing final assay results, and gas permeability can lead to sample evaporation over time, which is particularly problematic during thermal cycling.

While a centrifugal cartridge described by Schuler et al. allows complete workflow integration on a single platform, the device comprised a single chamber for droplet generation, thermal cycling and IRV readout, which requires fabrication of complex pyramidal structures with defined inclination angles within the chamber floor to allow IRV monolayer formation required for imaging as well as gas bubble removal. This increases the complexity of device fabrication, and further only provides a limited surface area for monolayer formation. Only 500 IRVs were read out in the imaging chamber, which is an order of magnitude lower than a minimum required for most assays.

There is therefore a need for centrifugal microfluidic chips, devices, and techniques for IRV generation, treatment and imaging, especially: compact, operator friendly, robust and precise systems; and chips fabricated in materials compatible with mass manufacturing techniques like thermoplastics and thermoplastic elastomers.

SUMMARY OF THE INVENTION

Applicant has devised a complete protocol sample to answer, on a low-footprint, low power consumption, centrifugal microfluidic system, that may be made at low cost, and may even be made portable. The system can have a footprint of less than 30×30×30 (cm); can operate on a range of microfluidic sample volumes that can be reliably dispensed; and is suitable for more complete automation. The system essentially consists of a general purpose centrifugal microfluidic device, with a suitably provisioned and loaded chip. The general purpose centrifugal microfluidic device can be used for a number of alternative purposes, especially if the centrifugal microfluidic device is equipped with controlled pressure supplied ports making it a P-blade platform, or at least having a pneumatic slip ring or rotary coupling for pressurized fluid transmission for stator-based control over pressure supplied at one or more ports of the chip.

The suitably provisioned chip has a network of chambers and interconnecting channels including: a treatment chamber (tc); a presentation chamber (pc); a sample path for delivering a sample to the tc; and a retraction path coupling a retraction chamber (rc) to the pc. The network is provided by relief patterning of (at least one) substrate on at least one side thereof, and sealed covering of the relief patterned surface with another substrate or a simple cover. The chip has a window that is transparent to inspection wavelengths, to permit imaging of the pc across a length and width thereof, either through the covering or the substrate, and preferably not through several layers of substrates and covers. The window may be substantially the whole cover, or substrate, and may be undifferentiated and unmarked, effectively allowing for imaging of any part of the network in view.

The suitably provisioned chip has: a nozzle in the sample path for producing IRVs from a sample and immiscible fluid, which may be one or more nozzles at the entry of the tc; a relatively deep tc that allows for treatment of the IRVs while in a 3D lattice or packing that is substantially more robust than 2D packings; a shallow pc for monolayer imaging; and a low resistance opening between the pc and tc to convey IRVs intact. Specifically, the nozzle has a hydrodynamic radius $r_n$ of 2-120 μm, adapted to deliver the sample to the tc discretized, as emulsion-divided IRVs surrounded by an immiscible fluid.

The tc has: a mean length ($l_{tc}$), defined by a ray from an intended axis of rotation of the chip, that intersects the tc to a greatest extent; a mean width ($w_{tc}$) in a plane of the chip perpendicular to $l_{tc}$; and a mean depth ($d_{tc}$) in the relief direction, as do the pc and the opening, respectively denoted: $l_{pc}$, $w_{pc}$, $d_{tc}$, $l_o$, $w_o$, $d_o$. As would be expected by those skilled in the art, $d_{tc} < l_{tc}$, $d_{tc} < w_{tc}$, $d_{pc} < l_{pc}$, $d_{pc} < w_{pc}$ and $d_o < w_o$. A volume of the tc ($v_{tc}$) would typically be from 10 to 800 μL, depending on the application, although further decreases are anticipated with increasing accuracy of the nozzle to define IRVs with smaller, regular radii ($r_{IRV}$). To ensure the emulsion can withstand treatment, $d_{tc}$ is between $5 \times r_n$ and 2 mm. To present a monolayer, $d_{pc}$ is $1.2 \times r_n$ to $7 \times r_n$, more preferably $1.6 \times r_n$ to $6 \times r_n$ and $d_{tc} > 2$ $d_{pc}$, more preferably $d_{tc} > 3$ $d_{pc}$, or $d_{tc} > 5$ $d_{pc}$. So $d_{pc}$ may be $1.5 \times r_{IRV}$ to $3 \times r_{IRV}$, more preferably $1.6 \times r_{IRV}$ to $2.8 \times r_{IRV}$, or $1.8 \times r_{IRV}$ to $2.5 \times r_{IRV}$.

The opening has a minimum hydrodynamic radius greater than $8 \times r_n$, and smooth perimeter walls, which can be planar or gradually arced. In general, the closer to a smooth cylindrical wall as a perimeter, the closer to a minimized perimeter to cross-sectional area, the less resistance is offered to flow therethrough, and the least shear stress the IRVs will be exposed to. Flat smooth walls of a slit were found sufficient.

The pc may have a wide footprint area of at least 1×3 (cm), for imaging e.g. at least 1000 IRVs (at least 5000 are called for in some assays, and at least 10-12K are called for in others), and may have a volume of 0.6-2 times that of the tc, so that the whole emulsion can be imaged at once. Alternatively, the pc may have a smaller footprint area, and allow for serial imaging of the IRVs, saving space on the chip, and obviating need for transporting the delicate IRVs a greater distance. The pc is aligned with the window for imaging of the IRV assembly.

The depths of all channels, and chambers other than pc, may be the same, as this can be convenient for designing and fabricating the chip, and efficiently uses footprint of the chip. As $d_{pc}$ may be small enough relative to its footprint area, the film and cover may be insufficiently stiff to ensure a satisfactorily constant working depth over a range of expected pressure differences between the ambience external to the chip, and within the pc. It is well known to reinforce chips with an array of pillars inside the chip, and/or with external structures. This need for reinforcement is reduced with: increasing $d_{pc}$; reduced pressure differentials between pc and ambient; and a reduced footprint of the pc. None of these may be amenable to reduction if all IRVs are desired to be imaged at once in the pc. If so, pillars or other support structures, can be used to support the pc ensuring $d_{pc}$ is maintained within parameters.

Alternatively the pc may provide imaging of a small fraction of the IRVs at any instant, but rather parades the IRVs across the pc. If so, reinforcements may be avoided, and an aspect ratio can be provided that is more extreme, such as a length (in the radius from axis direction) that is $\frac{1}{5}^{th}$ the width or less. Measuring colour variations in a plurality of successive photographs does pose some issues with respect to accuracy of counts, if the timing between the photographs are too long relative to the traversing rate, however, motion of the IRVs that is slow enough to allow for inexpensive, low shutter-rate imaging with substantial overlap in images, allows for multiple images to be taken and registered of each IRV. Furthermore, much smaller frame rate capture may be used for statistical purposes or recordal of the test. Image analysis of the photographs in sequence can also provide higher accuracy assessments across an imperfect, or intentionally varied spatio-temporal illumination patterns: for example some IRV colour states may exhibit better contrast in some lighting bands and others better in other bands.

By increasing $w_{pc}$, more IRVs are imaged per frame, and a minimum $l_{pc}$ is dictated by the imaging scheme. If 80% of the IRVs are only imaged once, and 10% overlap is all sufficient for identification of multiply imaged IRVs, the 10% may be a full bottom row of a 10 row pc, in which case, $l_{pc}$ may be $20 \times r_{IRV}$. By providing a ramped or stepped decrease in depth across the opening, and possibly an increased width as a function of distance from the tc, a shearing strain on the emulsion can be reduced given the requisite difference in depths of the tc and pc, and the extent of IRV rearrangement required to adapt to monolayer format for presentation.

The tc dimensions, particularly $d_{tc}$, chip may allow for thermal cycling to temperatures of at least 99° C. without observed collapse of IRVs, when fully surrounded in a suitable medium, such as a heavy oil (i.e. denser than the sample). The system is preferably designed for intimate contact of the chip with a heater or other energy transfer device (e.g. ultrasonic, acoustic, electromagnetic or thermal), preferably providing close contact between the cover or substrate that partially defines the tc and the device.

The centrifugal microfluidic system allows for sample to answer testing, such as genetic testing of emulsion-divided Independent Reaction Volumes (IRVs). Most prior art references refer to IRVs as "droplets", a term which may seem non-descript, lacking in teleological character, and unclear in that the whole sample may be the volume of a droplet. Specifically, the invention solves a problem of having to either avoid treatments of IRVs that tend to result in their coalescing, which typically are essential to many assays, or provide a very limited surface-area monolayer IRV pc, because moving an IRV ensemble in microfluidic chambers has been observed to collapse IRVs.

Applicant made many attempts to displace IRV ensembles that failed. The invention resolves this problem by moving the IRV ensemble, even if a large ensemble, from a high depth tc into the monolayer depth pc, without collapsing the IRVs while under centrifugation. As a result, centrifugal microfluidic systems, and especially pneumatically assisted centrifugal microfluidic systems, such as those described in the P-blade patent, can be leveraged for production, treatment and presentation of IRVs.

Applicant has discovered that, with the right interface between the tc and pc and a sufficiently low pressure applied at a corresponding port of the chip to drive the displacement, the emulsion can be displaced without substantial loss. An unprecedented number of IRVs have been imaged in a centrifugal microfluidic system: the system is automatic once the samples are loaded onto a chip, and the chip is coupled to a chip controller. A suitable opening between the pc and tc allows for the displacement if suitably controlled pressure is applied.

One advantage of the use of the P-blade platform, over non-pneumatically assisted (i.e. classical) centrifugal microfluidics, is that a dimension of the IRVs can be precisely controlled by varying both centrifugation rate, and applied pressure, as explained by Applicant in a paper entitled "Bouyancy-driven step emulsification on pneumatic centrifugal microfluidic platform" Lab on Chip 2020, 20, 3091, Jun. 22, 2020. Specifically the paper shows a chip arrangement in which the IRV diameter can be varied by at least 50 µm with a variation in centrifugation of 300-700 rpm, and an applied pressure of 0-40 kPa above ambience. The entire contents of this paper, and all supplemental disclosures thereof, are incorporated herein by reference.

Accordingly a centrifugal microfluidic chip is provided for mounting to a centrifuge for rotation about an axis, the chip comprising a network of chambers and interconnecting channels including: a treatment chamber (tc) having: a volume ($v_{tc}$) of 10-800 µL, and a mean length ($l_{tc}$), mean width ($w_{tc}$) and mean depth ($d_{tc}$), with $d_{tc} < l_{tc}$, and $d_{tc} < w_{tc}$; a first path for delivering a sample to the tc, the first path comprising a nozzle having a hydrodynamic radius $r_n$ of 2-120 µm, adapted to deliver the sample to the tc discretized, as emulsion-divided independent reaction volumes (IRVs) if the nozzle is filled with a suitable medium; a presentation chamber (pc) coupled to the tc by an opening through which the IRVs can be selectively displaced from the tc to the pc; a window transparent to a wavelength for inspecting the pc, provided through the chip at least across a length and width of the pc; and a retraction chamber (rc) coupled by a second path to the pc, wherein: $d_{tc}$ is between $5 \times r_n$ and 2 mm; the pc has a thickness $d_{pc}$ of $1.2 \times r_n$ to $7 \times r_n$; $d_{tc} > 2 \, d_{pc}$; and a flow path through the opening has a minimum hydrodynamic radius greater than $8 \times r_n$.

The pc may have a volume ($v_{pc}$) of 0.6 to 1.2 $v_{tc}$, a footprint of 3 cm² to 80% of a footprint of the chip. The network of chambers and channels may be produced in relief on at least a first side of a first film having a nominal thickness between 20 µm and 5 mm, and the chip may comprise a covering film that covers the first side to enclose the chambers and channels, away from ports of the chip. The pc may include an array of supporting microstructures to ensure that $d_{pc}$ is nominally maintained despite a pressure within pc, relative to ambient.

The nozzle may be located at an entry of the first path to the tc. The first path may branch to provide one or more additional instances of the nozzle.

The opening between tc and pc is preferably wider than long. The opening may comprise a ramp with a depth varying from $d_{tc}$ to $d_{pc}$, or one or more steps of depth intermediate $d_{tc}$ to $d_{pc}$. The ramp may have a slope of 30° to 75°.

The chip may comprise a stack of two or more films, at least one of the films having a relief structure defining the network, wherein: each film has a nominal thickness between 20 µm and 3 mm; each film is composed of a cured or set polymeric compound other than a siloxane; the chip has a thickness of 0.1 to 12 mm; the chip has planar extents of 3 to 25 cm; or the chip has at least 2 ports.

The first or second path may comprise a metering chamber with an overflow chamber, for volume-controlled delivery.

The chip may be loaded with one or more of: a sample-ready reaction mix, such as a PCR mix, in dried or liquid form in a first chamber within the first path; a sample in dried or liquid form, in a second chamber within the first path; a buffer, solvent, or liquid for dissolving, or suspending the sample or reaction mix within the first path; a dispersion medium adapted to support IRCs loaded within the tc, pc, or dc, to form a microfluidic system. The system may further comprise a low density medium in a chamber of the chip, the low density medium coupled to the tc by a third path that meets the tc at an axis-proximal end of the tc, the low density medium chamber loaded with a liquid having a lower density than that of: the sample, buffer, solvent or liquid, and dispersion medium.

The chip may be encased in a cartridge, the cartridge having a rigid structure for ease of manipulation and registration, while providing access to ports of the chip, and avoiding occlusion of vents of the chip.

The chip may be supplied in a kit with a chip controller, mounted, or for mounting to, a centrifuge, for rotation of both the chip and controller, the chip controller comprising an off-chip flow control device for selectively displacing fluid in the pc into the dc during centrifugation. The flow control device may comprise a pressurized fluid supply line for coupling to a port of the chip. The chip controller may comprise a chip holding surface dimensioned to support the chip on one side thereof, the chip holding surface comprising an energy device for selectively exposing the treatment chamber of the chip to an energy field. The energy field may be a thermal energy source or sink powered by an ultrasonic transducer or an electromagnetic field generator, in contact with chip adjacent the treatment chamber. The may further comprise a lighting and imaging system for imaging the pc, during centrifugation, or when the chip is at rest. The kit may be assembled to form a centrifugal microfluidic system.

A method is also provided for co-treating emulsion-divided reaction volumes (IRVs) and presenting them in a monolayer, the method comprising: providing the IRVs in a treatment chamber (tc) of a centrifugal microfluidic chip; applying an energy treatment to the IRVs within the tc, by activating an energy device mounted with the chip on a centrifuge while the chip is centrifuged, the tc having a minimum dimension that accommodates 3 to 100 IRVs; and operating a flow control device to displace the IRVs from the tc to a presentation chamber (pc) via an opening having a width greater than a mean diameter of the IRV, and a depth of the pc, to arrange the IRVs in a substantial monolayer, the flow control device applying a pressure difference of less than 15 kPa.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1' is a strip showing 6 stages of a process for forming IRVs, treating them, and then displacing them into a tc using the chip of FIG. 1;

FIG. 2' is a strip showing an enlargement of the view of FIG. 2 in 4 steps in a process for forming, treating and presenting IRVs;

DESCRIPTION OF PREFERRED EMBODIMENTS

Herein a centrifugal microfluidic technique (including a chip, cartridge, kit, system, and method) is described that allows for sample-to-answer testing, such as genetic testing of emulsion-divided Independent Reaction Volumes (IRVs). Specifically, the chip, the chip with loaded fluids to form a microfluidic system, a cartridge supporting the chip and facilitating mounting to a centrifuge or chip controller, a kit with the chip and a chip controller, and assembled kit to form a centrifugal microfluidic device, address the problem of how to displace an array of IRVs from a treatment chamber (tc), having a depth required to ensure the IRVs are in a 3D arrangement that makes them far more resilient to thermal treatment, into a monolayer-depth presentation chamber (pc) for imaging; the displacement inducing less or substantially less destruction of IRV division.

Centrifugal microfluidic systems, and especially pneumatically assisted centrifugal microfluidic systems, such as those described in aforementioned WO 2015/132743, including therein-identified prior art rotary couplers/pneumatic slip rings, that allow for pressure control at one or more ports of chips during centrifugation, are capable of supplying a controlled pressure and centrifugal field that cooperate to permit the displacement of dispersion medium and IRVs from the tc to the pc, with excess dispersion medium falling into a retraction chamber (rc).

Figures 1, 1A, 2, 2A, 3:
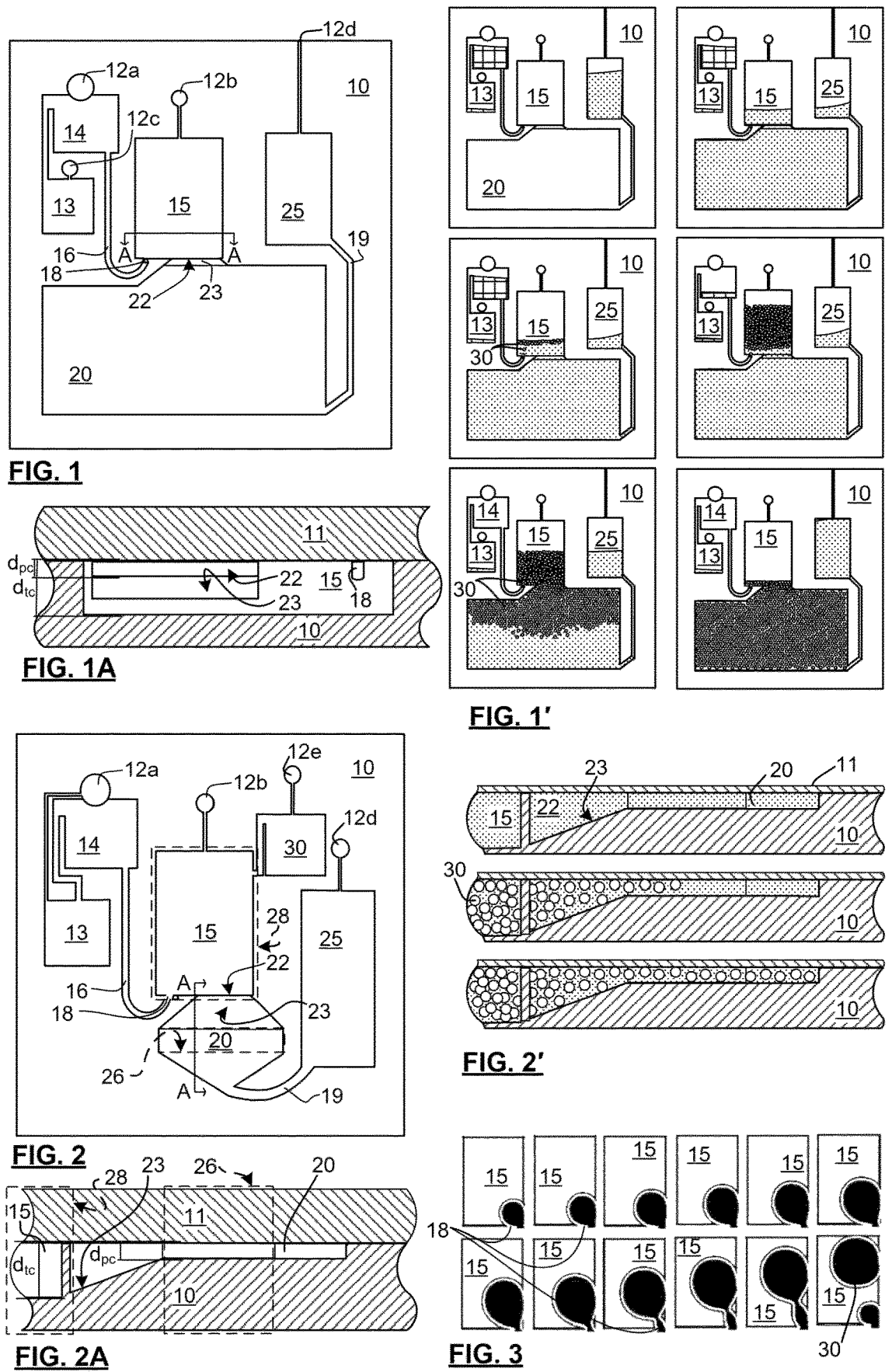
FIG. 1 is a schematic top plan view of a patterned substrate for a centrifugal microfluidic chip, according to a first embodiment of the present invention.
FIG. 1A is a partial cross-section view of the chip of FIG. 1 with a cover, featuring a wall commonly providing an outlet from the tc to a pc, and nozzle.
FIG. 2 is a schematic top plan view of a patterned substrate for a chip, according to a second embodiment of the present invention, with a smaller pc.
FIG. 2A is a partial cross-section view of the chip of FIG. 2 showing a depth transition of the opening between the tc and pc.
FIG. 3 is a strip illustrating in 12 steps how an IRV is formed and detached from a nozzle, to form an IRV.

FIG. 1 is a schematic illustration of a patterned film 10 of a chip, offering a simplified embodiment of the present invention. The chip is formed by film 10, and a suitable cover, which is not shown to permit viewing of the microfluidic network defined in relief pattern on a side of the film 10. The relief pattern provides a network that allows for a method of the present invention, and little more. More complex protocols call for more chambers and channels, which may require multiple, interconnected films. It is known to provide chips as stacks of layers with vias for interconnecting the layers to accommodate more complicated protocols. Alternatively, and equally, film 10 can be understood to be a single layer of a multilayer chip with a sample port 12a taken to be a via from another layer of the chip, for example, where the sample is prepared.

Typically chambers are vented, which means there is a respective vent 12 fluid coupled to the chamber. Vents may equally serve as a loading port, particularly if the chamber is designed to have a respective liquid loaded therein at the start of a protocol. As the term is commonly used, 'port' is any opening to ambience on a chip, whereas a vent, via, loading port, or pressure controlled/pressure supplied port specify intended function for the port: a vent allows fluid levels to rise (move axis proximally) or sink (move axis distally) in a chamber without trapping (compressing or extending a fixed volume air plug); a via communicates with a through hole to another chip layer; and a loading port is a port that allows for introduction of the liquid into the chamber (often this is performed while the chip is at rest, although there are some processes for off chip loading during centrifugation, as explained, in aforementioned WO 2015/132743). A pressure controlled port is a port coupled to a pressure supply, which may be coupled to the chip via a slip ring (fluid coupling rotary joint) or to a pressure supply chamber of the chip controller, which may be (mounted) pump fed, or a pressurized canister, if not supplied via a slip ring. In some cases, the pressurized fluid supply can be ambient pressure: before a valve is opened, the chamber may be in a positive or negative pressure state, e.g. in view of air plugs within the network, and opening the valve can discharge this pressure. Equally, closing an open valve can cause positive or negative pressure to build up as a result of centrifugation. Typically the pressure is supplied via a gas, although a liquid could be used in principle.

The chip, in accordance with the present invention, comprises a treatment chamber (tc) 15, a presentation chamber (pc) 20, and a retraction chamber (rc) 25, although they don't have to be arrayed as illustrated. The chambers are interconnected by channels and paths comprising one or more channels and possibly further chambers. Specifically, a delivery path is provided to deliver a sample to the tc 15, and a retraction path is provided between the pc 20 and rc 25 through which a fluid may be dispensed into the pc 20 and is withdrawn therefrom.

The delivery path shown in FIG. 1 comprises the sample port 12a which feeds a sample chamber 14 that has a spillway to an overflow chamber 13 vented via port 12c. The sample port 12a is enlarged compared with other ports, to facilitate sample loading. For example, it is logical for chips to have smaller loading ports for reagent loading in a controlled environment, for example with machines for alignment and automated injection (which may have be performed at vent 12b or 12d with respect to medium), and larger loading ports for manually supplying a sample or other fluid injected by a user.

By providing the sample chamber 14 with a spillway, a volume of the sample may be introduced in excess of a desired volume, without precise prior quantification of the sample volume. The excess volume will overflow the sample chamber 14 once centrifugation is applied, and the remainder in the sample chamber 14 will be efficiently metered to some precision.

The sample chamber 14 is coupled, via a J-shaped channel 16, to the treatment chamber 15 for sample delivery. In some embodiments it is preferable to provide a flow control device for stopping or starting the delivery, and/or controlling a delivery rate of the sample, although none are illustrated in the present embodiment except pressure controlled port 12a. The J channel 16 meets the tc 15 at a nozzle 18, although, in principle, the nozzle 18 can be supplied at other locations within the delivery path. For example, Applicant's U.S. Pat. No. 10,836,918, and its cited prior art references, teach microfluidic structures for in-line production of encapsulated droplets. In-line production could be used to generate IRVs further up the delivery path, and different IRVs can be subjected to different treatments prior to entering the tc 15 in alternative embodiments.

The nozzle 18 has a hydrodynamic radius $r_n$ that is the single most determinative feature of the chip's intended IRV size. For typical centrifugation rates, and pressures, the IRV's mean radius ($r_{IRV}$) is between 1 and 5 times $r_n$ and more typically about 1.1-3.5 $r_n$, or 1.2-2.8 $r_n$. As IRVs are not part of the chip itself (though it may be part of a system), $r_n$ is used for characterizing the chip claims.

The nozzle 18 is therefore adapted to dispense the sample into the tc 15 by dividing it up into IRVs, when the tc is partially filled with a denser, immiscible fluid, such as an oil. The tc is vented (12b) and provides a volume for accommodating an emulsion of the IRVs. If optimal, the medium will fill the tc minus the volume metered by sample chamber 14, and there may be a fill line on the substrate or cover to mark this.

A depth of the tc ($d_{tc}$) is preferably at least 5 times a mean radius of the IRVs ($r_{IRV}$) for which the chip is designed, although in principle it could be as small as 3.5 times $r_{IRV}$ and still function for distributing the IRVs in a 3D packing lattice. The pc has a depth ($d_{pc}$) of 1.3-3.2 $r_{IRV}$, more preferably 1.6-2.5 $r_{IRV}$, or 1.8-2.3 $r_{IRV}$. Understood with respect to $r_n$, instead of $r_{IRV}$, $d_{pc}$ is 1.3-15 $r_n$ as the outside-outside range, and 2.16-8.05 $r_n$ as the most preferable range, although all intermediate ranges of all ranges herein are intended. As $r_{IRV}$ might range from 30-150 μm, more typically 40-110 μm, and currently typically 50-100 μm, to encourage monolayer arrangement, $d_{pc}$ is 48-450 μm to 95-230 μm, with all the intermediate ranges herein intended. With the advances of technology, smaller IRVs are anticipated, calling for smaller $r_n$ and $d_{pc}$.

The opening 22 between the tc and pc is a slit that accommodates the change in depth between $d_{tc}$ and $d_{pc}$ with a ramp 23, that is best appreciated having regard to FIGS. 1 and 1A together.

FIG. 1A shows a partial cross-sectional view from line AA of a chip that includes the film 10 and a covering layer 11. This view features an axis-distal wall of tc, which shows both a nozzle 18 at a top edge thereof, and a change in depth of the opening 22 which extends between the tc 15 and pc 20. Specifically, a smooth ramp 23 is shown extending from a depth of approximately 0.3 $d_{tc}$ to $d_{pc}$; $d_{pc}$ is shown approximately ¼ $d_{tc}$, although a ratio of ⅛$^{th}$ to ¹⁄₁₀$^{th}$ $d_t$ may be more preferable for most applications. The smaller $r_{IRV}$, the smaller $d_{pc}$, but not necessarily $d_{tc}$. It will be appreciated that the ramp might have begun lower or higher than from 0.3 $d_{tc}$ as shown, and further that one, or preferably, more steps may be provided where a ramp is not easily formed. A density of the IRVs at different depths, may depend on a distance in the tc from the opening 22. If the cover faces up, the density of IRVs at the opening 22 may be lower below the (0.3 dtc) ramp 23's bottom edge due to gravity, if the medium is dense enough. Applicant finds the ramp is not necessary for good operation.

From FIG. 1, a run of the ramp 23 can be seen to be about 15% of a width of the opening at the tc 15, and the opening flares from the tc to the pc with an angle of about 38°. As such the opening expands continuously in one direction, while shrinking in the other. The partial compensation for the high degree of constriction in the depth direction by the expansion in the width direction, reduces a shearing stress on the IRVs during displacement across the opening 22. The substantial reorganization of the IRVs required to adopt a presentation monolayer from the 3D packing, can be accomplished by the engineering of the opening, with modest control over the centrifugation rate, and application of nominal pressure differences at the ports of the chip. It is an unexpected result that IRVs can pass this gate intact, while urged forward by pneumatic supply applied by the ports 12.

The retraction path includes a channel 19 coupling the axis-distal ends of rc 25 and pc 20, and a pressurized port 12*d* that allows for controlled fluid displacement between pc and rc. Port 12*d* is illustrated as an edge port, which may have advantages in chip assembly, and mounting for sealed coupling to pressure supplied ports. For example, if all ports are edge ports, manual coupling of various ports to various supply lines can be provided all at once by a suitable sealing structure with some tension, with minimal equipment, and adequate sealing.

The film 10 can be relief patterned in any of the ways known in the art, including by injection molding, thermoforming, 3D microprinting, and micromachining. Each of these forming routes have advantages and disadvantages that are economic chiefly depending on a volume of production, but some are particularly suited to producing channels and chambers having floors of relatively constant depths, and some require particular efforts to vary a depth within a single chamber. As such the pyramidal features required on the floor of the chamber described by Schuler imposes some limitations on forming that may make chips uneconomical at a required scale of manufacture. All methods provide different depths of different chambers.

FIG. 1' is a strip of 6 plan frames of the film 10 at successive steps in an IRV generation, treatment and presentation process. A top left frame shows sample in sample chamber 14 (with a small amount spilt into overflow 13) and heavy medium loaded into the retraction chamber 25. The sample is preferably a careful mixture of a biological fluid, or aqueous carrier of an air, water, food or soil sample (or a processed sample or fluid, such as a filtrate, retentate, lysate, fraction or other purification thereof) with a buffer; an all in one PCR (or like) reaction mix; and colorimetric targets or functionalized particles, as this will allow for ddPCR. This frame is consistent with the chip imaged after initial spinning, subsequent to loading and mounting on a centrifuge.

The second frame (top right) shows the heavy medium dispensed into the tc and filling the pc as the heavy medium would do under continued centrifugation if there is no blocking of port 12*d*. Port 12*d* could be coupled to a valve open to ambience to control a timing of the dispensing of the heavy medium, as in FIG. 12 of the P-blade patent, if timing is desired. Otherwise a continuous process of dispensing may start with centrifugation, as the sample adopts its position in the first frame. Centrifugation will naturally draw the sample through the J shaped channel 16 at a given rate, and the dense medium at another rate, but any race condition between these two fluids to the nozzle 18 is non-critical, as a hydrodynamic resistance in the J shaped channel 16 and nozzle 18 will prevent the sample from entering the tc 15, whether empty or full, until a pressure difference is applied at ports 12*a,c* relative to 12*b* to overbear the hydrodynamic resistance in the supply path. As a result, there will be an air plug between the heavy medium and sample that is ejected as bubbles through the oil before the sample is delivered through the nozzle 18, as shown in the third frame (middle left).

The third frame shows the first IRVs 30 forming, and buoyantly rising through the heavy medium. The heavy medium has a high surface tension and a contact angle suitable for encapsulating the sample. The IRVs rise and form a froth by flotation within tc 15. The IRV formation continues in the fourth frame (mid right), until the tc is substantially filled, or the sample chamber 14 is sufficiently empty. It is not advisable to allow any air bubbles to be introduced into tc 15 after the IRVs are formed, and it is therefore preferred either to allow visual (or machine vision) inspection of sample chamber 14 for manual or automated feedback-based control of the duration of applied pressure difference between ports 12*a* and 12*b*, in which case a second window may be provided for camera-based imaging of sample chamber 14. Alternatively, and more efficiently, as sample chamber 14 is metered, programmed control over the pressure supplies can be calibrated to dispense the volume with a provisioned time that allows a sufficiently low risk of excess ejection into tc 15. $d_{tc}$ ensures that the IRVs form a 3 dimensional packing within tc, and this affords a thicker set of webs of the heavy medium, separating adjacent IRVs more reliably than in a 2 dimensional packing.

The supply of heavy medium in tc 15 should also be assured. Heavy medium shown in the second frame is more than sufficient for initial IRV formation, however as the IRVs rise buoyantly the added mass of the sample will depress the heavy medium, raising the heavy medium level in retraction chamber 25. If the heavy medium level were to fall below the level of nozzle 18, the IRVs may continue to rise, but they could only be thinning webs of all of the IRVs, until some of the IRVs in a most depleted zone coalesce. Thus, in use, a preloaded amount of heavy medium initially fills pc, and sufficiently fills tc to ensure the fill level never falls below the nozzle 18. Another option is to monitor and control the heavy medium, for example by visualizing the tc 15, and selectively applying positive pressure at port 12*d* to apply a gentle push to lift the heavy medium before it falls axis distally of the nozzle 18 prior to collapse of the IRVs, and to stop the pressure at port 12*a* once the tc is replete. The monitoring may be preferred if there is a high variability of the volumetric ratio of IRV to the encapsulating liquid. This monitoring may be provided on-line with image analysis and feedback, or manually by a human operator.

Thus between frames four and five, the sample chamber 14 is emptied, all of the IRVs are formed, and the ensemble of IRVs is subjected to a thermal treatment. To this end, the blade to which the chip (or a cartridge bearing the chip) is preferably provided with a temperature controlled unit, such as a Peltier heater/cooler, or a thermal capture and conducting surface in close proximity to the tc 15. The thermal capture and conducting surface is preferably intimately close to the tc, and may have a built-in temperature sensor, but is preferably mounted to, and powered by, the blade or a chip controller thereof, as opposed to being part of, or permanently affixed to, the film 10 or chip, so that the chip is of a lower cost, disposable type. The film 10 or cover 11 may be selected for marginal improvement in thermal conductivity, however. The purpose of the thermal capture and conduction surface is to responsively heat the tc, for example via an on-blade laser, LED, or glowing bulb heat source or a strobed stationary laser, LED, or glowing bulb heat source intermittently aligned with the tc.

Once the thermal treatment is completed, retraction of the heavy medium, and the buoyantly entrained IRVs 30, is provided. The fifth frame shows this process begun, and by the sixth frame, the retraction is complete, retraction chamber 25 is replete, and a monolayer of IRVs is presented in the pc 20. The chip controller, or centrifuge may naturally have a camera for imaging the pc, which could, in some cases be mounted to the blade, although this might require specialized optics and illumination, or can be provided by a strobing light and camera within the centrifuge, or may further be provided for the chip after centrifugation. If the imaging is performed off centrifuge, or after centrifugation, the content of the chip may shift between its resting state during centrifugation and when the chip comes to rest, particularly if un-vented chambers are allowed to develop pressurized air plugs during operation. In the extreme this shifting may destroy IRV boundaries. A controlled deceleration of a chip (with or without pressurized air plugs) may effect the movement of the IRVs to the pc without damage.

Most aspects of the chip's microfluidic network are not essential, including the shapes, orientations, and dimensions of the chambers, layout of channels and ports, and materials or compositions of the layers (i.e. film 10 and cover 11). Herein variants of the first embodiment are provided to illustrate some variant features that may be varied in particular ways. These variants are generally understood as mutually independent in that any combination of the features can be assembled in respective embodiments of the invention.

FIG. 2 is a layout of a substrate 10 that varies in these principal respects: the pc is a flow-through chamber for videographic, or serial, imaging of IRV; and a light medium chamber is provided for topping off the IRVs in the tc, and reducing outgassing during heat treatment. FIG. 2 further illustrates in ghost view a heat treatment area 28 and window area 26 through which pc 20 can be imaged. Minor variations in chip layout are also provided, for example with ports 12*a,c* being joined.

The light medium chamber 30 is preferred for IRVs liable to volatilization during the heat treatment, such as aqueous samples. A capping light medium, such as an oil, has been found to be useful in preventing outgassing that would otherwise affect volume of the IRVs, dissolution of sample components, and impair reactions.

The flow-through pc 20 has a somewhat symmetric form in that both opening 22 and exit have symmetric flaring. As can be seen in FIGS. 2,2A the ramp 23 is much more gradual in the first variant, having a slope of about 20°. As $d_{tc}$ and $d_{pc}$ are comparable in the variant to the embodiment, this is accomplished by providing a run of the ramp 23 that is about 4 times longer. The flow through the opening 22 is expected to apply lower shear stress on the IRVs 30 in the variant: the transition from the 3D packing in the tc to monolayer in the pc is provided more gradually with this lower slope ramp 23. The ramp 23 ends at a beginning of the window area 26, and the beginning of the pc 20. While not necessary, flaring of the pc exit leading to the retraction channel 19 may reduce shearing force at the abrupt change in flow direction. It is substantially preferable to avoid any collapse of the IRVs prior to entry into the retraction chamber 25, where agglomerated aqueous IRV contents can rise buoyantly through the heavy medium without interacting with any IRVs in the pc.

To this end, the channel 19 may be further modified to provide smoother transitions for the IRV laden heavy medium.

FIG. 2A shows a marked partial cross-section shown on FIG. 2, of the chip consisting of the film 10 and a cover 11. FIG. 2' is a strip showing 3 steps in a process according to the present invention, each frame thereof showing an enlarged view of the chip of FIG. 2A with the tc, opening, and pc filled, respectively with heavy medium (top) in the first frame; with IRVs beginning to enter the pc in the second frame (mid); and with parading IRVs in the third frame (bottom). In order to operate the chip, it is mounted to a platform and is set to spin. The sample and heavy medium are displaced, respectively into the J channel 16, and to fill the pc, and come to a fill level within the tc (top frame). Once complete the heavy medium covers the nozzle in the tc, the sample is transferred to the sample metering chamber by applying a positive pressure at port 15*a* (with 15*c* blocked or co-pressurized) which is high enough to overcome the siphon valve that connects supply chamber 14 and tc 15. As the sample is transferred, the emulsification process starts as the nozzle 18 forces the sample to enter into the tc as discrete IRVs, which is further illustrated and explained hereinbelow with reference to FIG. 3. The IRVs are thus generated in the tc. Once the IRVs are made, light medium from chamber 30 is transferred to the tc by applying a positive pressure at port 12*e*. The light medium rises to the top of the chamber (due to lower density than the sample). The thermal treatment is then commenced by applying a set temperature (or a temperature cycling sequence) using a controlled heater. As the cartridge spins during thermal treatment, the emulsion is sandwiched between the heavy and light oils which prevents evaporation and maintains IRV stability. After the thermal treatment is completed, without stopping the centrifugation, the IRVs are transferred into the shallow pc 20 by applying a negative pressure at the port of the retraction chamber 25. The mid frame shows this beginning, and the bottom frame shows an arbitrary moment in the parade of IRVs across the window. As such, the first frame of FIG. 2' corresponds to any of the frames 2-4 of FIG. 1. The second frame shows how once sufficient dense medium is retracted into the retraction chamber 25, some of the IRVs are pulled into, and through the opening 22. Thereafter, the IRVs are paraded across the pc. This process is expected to take some time, as the displacements are slow and this facilitates imaging as well as the prevention of IRV collapse. Unlike the embodiment, the variant allows for accumulation of IRVs, or other poolings or collections of IRV content, in the retraction chamber 25.

FIG. 3 is a strip showing IRV formation at the nozzle 18. It should be noted that each of the 12 frames is displayed sideways, with the bottom edge of the frame corresponding to the axis-distal wall of tc 15, and the right edge corresponding to the surface of the cover 11. At each successive frame a larger volume of sample is injected into the heavy medium, and the buoyant force increases drawing the upwards as drawn (i.e. opposite the centrifugal field). By frame 9, the IRV can be said to be formed, but tethered to the nozzle by string of the sample. Buoyancy displaces the IRV further and further from the nozzle, drawing further sample into the tc, but the tether snaps at the 12$^{th}$ frame and the string of sample snaps back to a free-surface-energy favoured spherical shape, seeding the next IRV.

While FIGS. 1 and 2 show two embodiments having no features other than those which directly cooperate in the IRV formation and presentation process of the present invention, it will be appreciated by those of ordinary skill that many chips preferably perform multiple steps of sample preparation and treatment to produce the sample for testing. The chips of FIGS. 1 and 2 are suitable for any application that requires IRV generation, thermal manipulation and subsequent monolayer formation for imaging, including ddPCR, ddLAMP, ddRPA, or single cell based assays, where single cells are encapsulated with specific reagents, cultured for a specified time period and subsequently imaged. To control a maximum of one cell per IRV, the easiest way is to dilute the sample to an appropriate cell concentration that would, for a given sample and IRV volume, provide at maximum one cell per IRV as predicted by a Poisson distribution. For example, about 15% of IRVs would contain one cell, and other IRVs will only contain aqueous buffer and dissolved or carried particles and species. As will be appreciated by those of skill in the art, flow focusing and other techniques can be provided to control or arrange cells in a channel with specific spacing between them prior to reaching a nozzle that forms droplets.

Figures 4, 5:
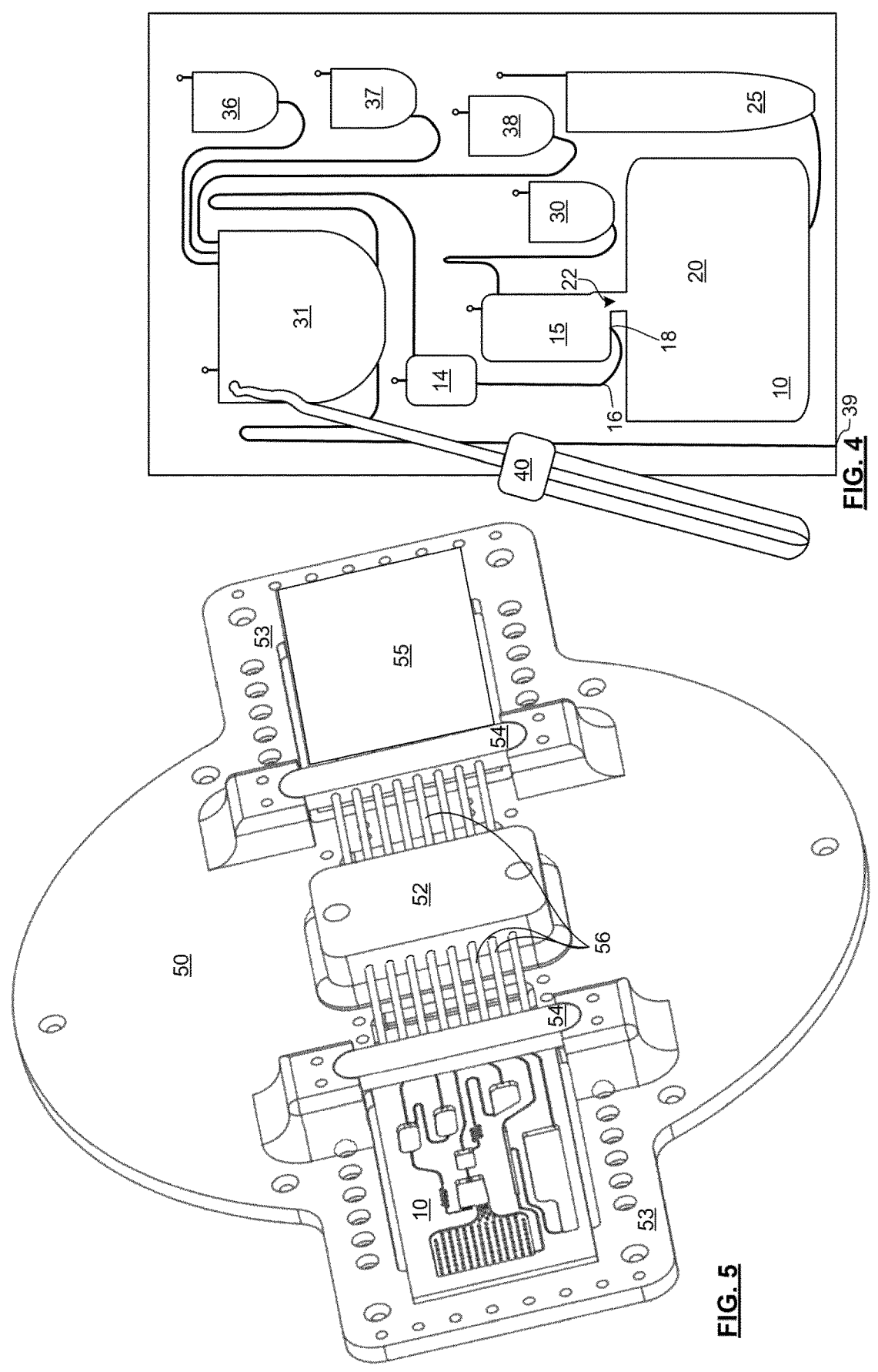
FIG. 4 is a schematic top plan view of a patterned substrate for a chip, according to a third embodiment of the present invention, with additional chambers for providing a complete ddPCR protocol.
FIG. 5 is a schematic view of a system comprising a chip controller, upon which a fourth chip embodiment is mounted.

FIG. 4 schematically illustrates a film 10 patterned to provide a chip for complete sample to answer assay, such as nucleic acid extraction from various clinically relevant biofluids, including blood, saliva, urine, etc. In addition to providing all the chambers and channels required for IRV generation, thermal treatment and presentation, additional chambers are provided for nucleic acid isolation from biofluids. As assembled for intended use, the sample chamber 14, is preloaded with a dry reagent, and the following chambers are loaded, respectively with: heavy medium in the retraction chamber 25; light medium in chamber 30; binding buffer in chamber 36; wash in chamber 37; and elution buffer in chamber 38. The binding buffer, wash, and elution buffer chambers 36-38 are coupled to a mixing chamber 31 containing a bed of beads, the beads functionalized for nucleic acid extraction. Mixing chamber 31 is provided for sample lysis. Furthermore there is an off-chip sample vial 40 coupled by tubing to the mixing chamber 31. The mixing chamber 31 is also in fluid communication with sample chamber 14, and an off-chip waste reservoir 39, as taught in Applicant's co-pending WO 2020/100039.

Sample is transferred to mixing chamber 31, and binding buffer is also transferred to chamber 31 by applying a positive pressure at chamber 36 via its respective port. The binding buffer lyses the sample, extracting nucleic acid from the sample. The functionalized beads (preferably porous, high surface area beads such as silica), preferably assisted with temperature control provided by Peltier device, capture the nucleic acid. Next, the liquid content of chamber 31 (unbound lysate) is drained by applying a positive pressure at mixing chamber 31's port for a period long enough to prime a channel to the off-chip waste 39, but not long enough to prime a channel to the sample chamber 14. As a diameter of the beads is greater than a diameter of the mixing chamber's opening to the off-chip waste 39, the beads are retained while the unbound lysate exits. The chamber 31 is then washed at least once, by displacing wash into the chamber 31 and again draining chamber 31. The nucleic acid template is eluted from the beads by transferring the elution buffer into chamber 31. This may involve heating the mixing chamber 31 to facilitate release of the nucleic acid. Next, the eluted template is transferred to sample chamber 14, for example by applying a negative pressure at ports 12a,b,d with sufficient pressure and duration to overcome a siphon valve connecting chambers 31 and 14. This channel with the siphon valve, sample chamber 14, and the J channel with the nozzle 18 at the tc 15 form the delivery path in the present embodiment. At this juncture the elution buffer, carrying the nucleic acid, fills sample chamber 14, hydrating and dissolving the dried premix. If helpful, pressures applied at ports 12a,b,d can be applied to induce bubble-mixing of the sample, to ensure adequate dissolution and sample homogeneity. Once this is complete, the process for emulsification, heat treatment, and presentation can start as in previous examples.

FIG. 5 is a particular instance of a centrifugal microfluidic system for thermal treatment and display of emulsion-divided IRVs. The system comprises a centrifugal blade 50, adapted to mount to a centrifuge about an axis (not in view). The blade 50 comprises two chip receiving parts 53 at opposite ends, and a flared, or rounded, plate body extending substantially midway between the chip receiving parts 53. The flared plate body section provides a location for applying masses to balance the centrifuge.

Two chips 55 are designed to be mounted to the blade 50 at the chip receiving parts 53, although one instance shows the cover removed for illustration (i.e. patterned film 10). It will be noted that frequently chips are reinforced to form cartridges, as these tend to facilitate manipulation, and avoid displacing preloaded fluids by unintentional manipulations of the chip, and for precision alignment of the chip with corresponding features of the blade 50, such as heating systems, viewing systems, and pressure supplied ports; however structures to provide such reinforcements tend to occlude the chip and have been omitted.

At the centre of the blade 50, is a controller 52, which may have electrical circuitry, a power supply, a pressurized fluid source, a pump, a flow control element, or a pneumatic, hydraulic, and/or electrical slip ring for supplying a fluid, or electrical power or signaling, to control pressure supplied to respective fluid supply lines 56, eight of which are shown. A supply coupler 54 couples respective ports 12 of the chip to respective fluid supply lines 56. The two instances of the chips may be performing duplicate testing, or may have different sample sources, running the same test, for example, but typically have duplicate pressure supply lines 56 for co-operating both chips at the same time.

Figures 5A, 5B:
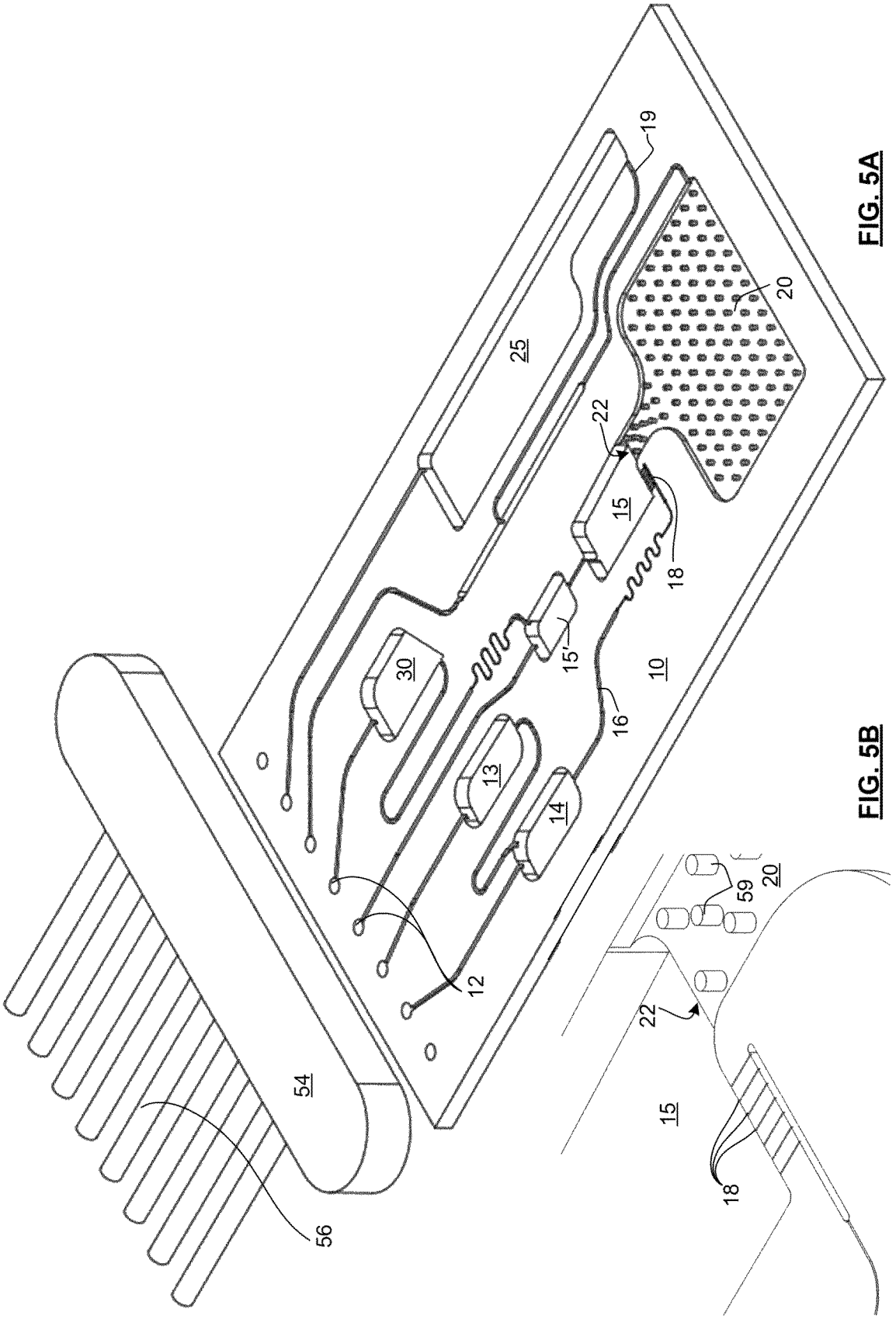
FIG. 5A,B respectively providing enlarged views of the chip, and of an array of nozzles meeting the tc, and an array of supporting microstructures in the pc.

FIG. 5A shows the film 10 according to a third variant, with the coupler 54 exploded to afford a complete view of the film 10. In the third variant, there are some minor alterations. For example, instead of chamber 13 being an overflow chamber, it is a separate chamber for dry reagent into which a raw sample is provided. The sample provided into the chamber 13 prior to centrifugation, dwells with the dry reagent long enough for mixing by diffusion, and is metered into sample chamber 14 by control over chamber 13's port. The J channel 16 has a hydrodynamic resistance, and opens to an array of nozzles 18, as is better illustrated in FIG. 5B. The tc 15 has an overflow 15' providing buffer space for light medium that is supplied from chamber 30 through a hydrodynamic resistance that improves control over dispensing rates. The fact that introducing the sample into the tc causes expansion of the occupying volume of the tc, while also displacing heavy medium back into the retraction chamber 25 leads to provisioning issues about this volume. While light medium helps address a difference in volume, an ability to overfill the tc to the point that the light medium is substantially removed from the tc, without entraining any IRVs, is advantageous. In alternative embodiments, the light medium may be returned to chamber 30 instead of displacing air in the overflow chamber 15'. The heavy medium chamber 25 is provided with a vented metering channel, to more accurately dispense a volume of the heavy medium. The metering channel provides a useful location for verifying a fill level of the heavy medium within the tc during centrifugation, prior to IRV formation. The pc 29 is shown with an array of pillars for supporting and reinforcement. As the $d_{pc}$ is very small, the pillars are necessary to prevent the variations in pressure on the chip from substantially altering the depth in use. These are better illustrated in FIG. 5B.

FIG. 5A also shows how a single clamped structure can press each of the provisioned ports of the chip 55 into sealed connection with respective supply lines 56 via coupler 54.

FIG. 5B show a partial enlarged view of a particularly sensitive part of the patterning of film 10 according to the third variant. There are seven nozzles 18 that are shown coupled with an expanded manifold segment of J channel 16, after the hydrodynamic restriction. Thus the sample pressed through the restriction floods the manifold, and distributes about equal flow rates to each of the 7 nozzles. Not far away, the opening 22 is shown, and pillars 59 disposed in the pc 29, and extending right to the opening 22 are in view. The pillars 59 have dimensions, pitch, and offset to minimize flow interaction with the IRVs, and to avoid shear stresses within the flow.

EXAMPLES

Figures 6, 7, 7A, 8:
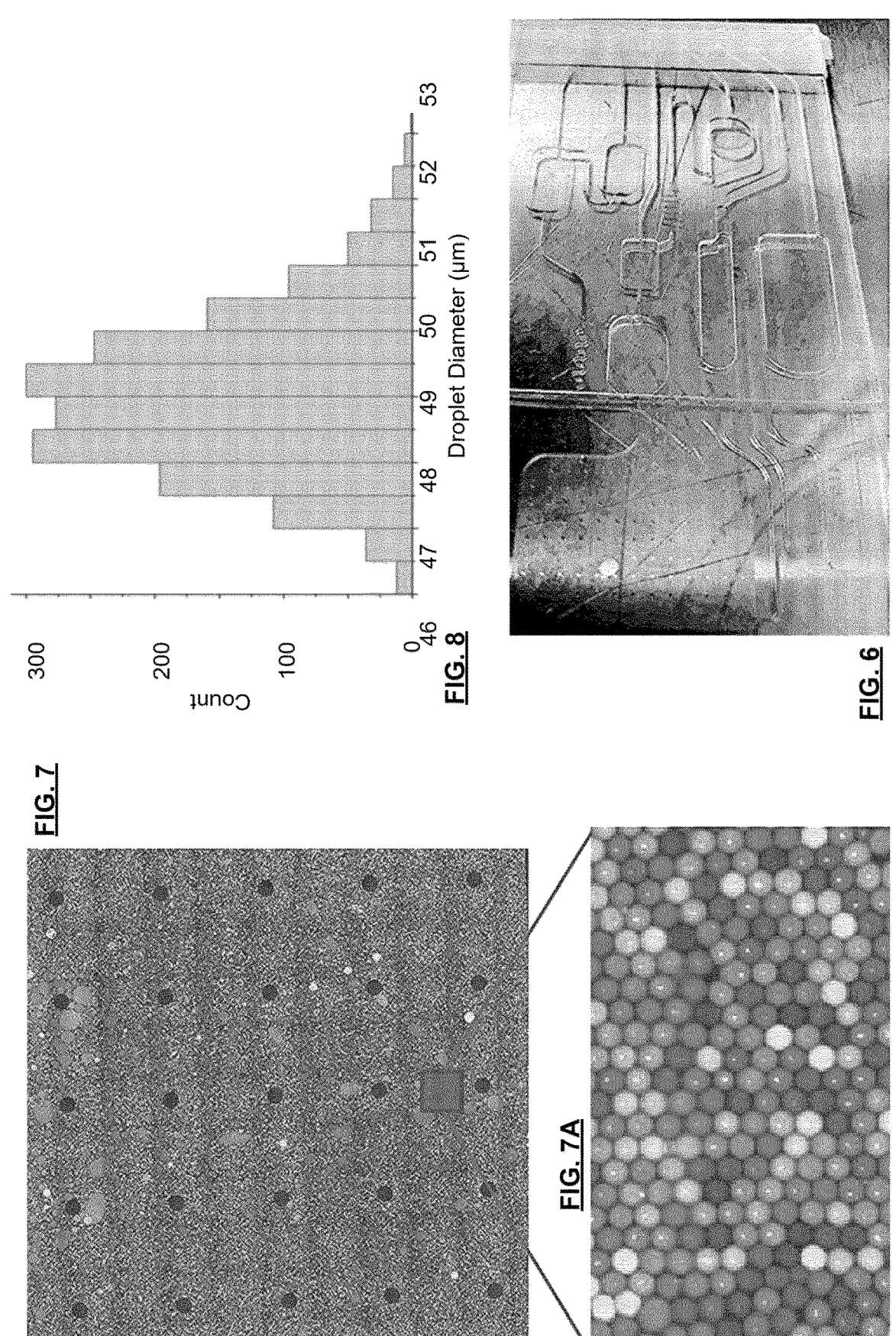
FIG. 6 is a photograph of a chip used to demonstrate the invention.
FIG. 7 is a photograph of the presentation chamber, acquired during centrifugation.
FIG. 7A is an enlargement of a small area of the image.
FIG. 8 is a bar chart showing IRV diameter distribution of an ensemble produced using an example produced to demonstrate the invention.

The invention has been demonstrated by a number of experiments. FIG. 6 is a photograph of a chip used to test the invention. The patterning is most alike the third variant, and it has a large pc provided with a view to presenting all IRVs at once for imaging. It was fabricated in a thermoplastic elastomer (Mediprene OF™), by hot embossing a film and bonding to a flat COC sheet. The device was subsequently used to generate the IRVs with the protocol described below, thermal cycle the emulsion, and to transfer the emulsion to the pc. On this chip, $d_{pc}$ was 60 μm and $d_{tc}$ was 500 μm.

Initially, the chip was filled with all the required liquids to generate the IRVs and run droplet PCR. Specifically, 200 μl of heavy oil was loaded into the retraction chamber, followed by filling 20 μl of the sample (PCR mix with template) in chamber 13, and 20 μl of mineral oil was filled in light medium chamber 30. Next, the device is placed on a blade of a centrifuge with the inlets sealed with the pressure supplied ports of the blade, and the platform is rotated at 400 rpm.

A positive pressure of 1.5 psi is applied at port 7 (in the examples section, all ports identified numbered left to right on FIG. 5B, or 6) to transfer heavy oil to pc, opening and tc until tc 15 (not overflow 15') is completely filled. Next, the rotation speed is increased to 600 rpm. At this juncture, the tc content went down to about half fill tc. Subsequently, the sample is transferred from the chamber 13 to sample chamber 14 by applying +1 psi, pulse at port 3, for 200 ms.

With the sample in chamber 14, the IRVs can be generated in the next step, by applying a constant pressure that is greater than +1.5 psi at ports 2 and 3 (and further controlling rotation rate), which is sufficient to overcome the resistance of the J channel, and initiate the process of IRV generation though the nozzles. The exact pressure and rotation rate, along with the provisioned hydrodynamic radius of the nozzle will dictate the IRV diameter and volume, which can be set on demand and customized to specific application. In this case the nozzle had a width of 10 μm, and a depth of 8 μm, and a hydraulic radius is therefore 2 (10×8)/(2(8+10)) which is approximately 4.5 μm.

Upon application of the pressure, the IRVs were generated to fill completely tc all the way to the overflow chamber 15', but no IRV entered the overflow chamber. This was important in order to avoid IRV collapse during thermal treatment.

Following IRV generation, light oil was dispensed into overflow chamber by applying a pressure of +1 psi at port 5. This step was used to prevent evaporation during thermal cycling and retaining IRV stability at the elevated temperatures required for the particular PCR process applied (i.e. 95° C.).

Next, a thermal cycling sequence was applied at a Peltier heater located on the blade below the tc. After the thermal cycling was complete, negative pressure of −1 psi was applied at ports 6 and 7 to start transferring the emulsion to the pc by retracting heavy oil. During this process, the rotation speed is slowly decreased (in 10 rpm increments) down to 300 rpm in order to prevent backflow of the oil into the pc once the platform stops spinning. Upon transfer completion, the pressure is turned off and rotation is stopped, allowing subsequent imaging of the IRVs.

FIG. 7 is a photograph of the imaged pc, with the array of supporting pillars shown as dark spots. While some banding of IRVs can be seen, and particularly near the top of the pc, some regions of IRV collapse are visible, the vast majority of the pc is filled with a substantially hexagonal packing of uniformly sized IRVs. Neighbouring IRVs have different coloration demonstrating the effective separation of the IRVs during heat treatment. FIG. 7A shows (a top) part of the enlarged area showing the tight hexagonal monolayer, each IRV independently reporting PCR fluorescent response.

FIG. 8 is a histogram showing IRV diameter counts, affording Applicant an opportunity to compute a mean and CV of the distribution, which respectively are: 49 μm, and 2.38%. This demonstrates that the volume of each IRV is sufficiently constant for most analyses. As noted in the LOC paper incorporated by reference hereinabove, the chip arrangements to produce IRV diameters with reasonably narrow distributions centred on a variety of diameters from a few microns to at least 100 μm, can be produced with a variation in centrifugation of 300-700 rpm, and positive pressure of 0-40 kPa.

The application of the proposed chip and system has been demonstrated for automated IRV generation, thermal cycling and emulsion transfer for imaging.

The essential features of the chip and system for heat treating, and displacing an emulsion of IRVs has been described herein with a minimum of view-obstructing alternative elements. It will be appreciated by those of skill in the art that a number of sensors, and devices can be added to the blade or chip controller provide additional process controls and feedback for further improvements. Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

REFERENCES

Malic, Lidija, et al. "Epigenetic subtyping of white blood cells using a thermoplastic elastomer-based microfluidic emulsification device for multiplexed, methylation-specific digital droplet PCR." Analyst 144.22 (2019): 6541-6553.

Schuler, Friedrich, et al. "Digital droplet PCR on disk." Lab on a Chip 16.1 (2016): 208-216.

Schuler, Friedrich, et al. "Digital droplet LAMP as a microfluidic app on standard laboratory devices." Analytical Methods 8.13 (2016): 2750-2755.

Li, Bin, et al. "Miniaturized Continuous-Flow Digital PCR for Clinical-Level Serum Sample Based on the 3D Microfluidics and CMOS Imaging Device." Sensors 20.9 (2020): 2492.

Hu, Fei, et al. "Smartphone-based droplet digital LAMP device with rapid nucleic acid isolation for highly sensitive point-of-care detection." Analytical Chemistry 92.2 (2019): 2258-2265.

Madic, J., A. Zocevic, V. Senlis, E. Fradet, B. Andre, S. Muller, R. Dangla, and M. E. Droniou. "Three-color crystal digital PCR." Biomolecular detection and quantification 10 (2016): 34-46.

Clime, Liviu, et al. "Bouyancy-driven step emulsification on pneumatic centrifugal microfluidic platforms." Lab on a Chip 20 (2020): 3091-3095.

Schuler, Friedrich, et al. "Centrifugal step emulsification applied for absolute quantification of nucleic acids by digital droplet RPA." Lab on a Chip 15 (2015): 2759-5766.

The invention claimed is:

1. A centrifugal microfluidic chip for mounting to a centrifuge for rotation about an axis, the chip comprising a network of chambers and interconnecting channels including:

a treatment chamber (tc) having: a volume ($v_{tc}$) of 10-800 $\mu$L; and a mean length ($l_{tc}$), mean width ($w_{tc}$) and mean depth ($d_{tc}$), with $d_{tc} < l_{tc}$, and $d_{tc} < w_{tc}$;

a first path adapted to deliver a sample to the tc, the first path comprising a nozzle having a hydrodynamic radius $r_n$ of 2-120 $\mu$m, adapted to deliver the sample to the tc discretized, as emulsion-divided independent reaction volumes (IRVs) if the nozzle is filled with a suitable medium;

a presentation chamber (pc) coupled to the tc by an opening through which the IRVs can be selectively displaced from the tc to the pc;

a window transparent for inspecting the pc, provided through the chip at least across a length and width of the pc; and a retraction chamber (rc) coupled by a second path to the pc, wherein: $d_{tc}$ is between $5 \times r_n$ and 2 mm; the pc has a depth ($d_{pc}$) between $1.2 \times r_n$ to $7 \times r_n$; $d_{tc} > 2$ $d_{pc}$; and a flow path through the opening has a minimum hydrodynamic radius greater than $8 \times r_n$.

2. The chip of claim 1 wherein the pc has: a volume ($v_{pc}$) of 0.6 to 1.2 $v_{tc}$; and a footprint between 3 cm$^2$ and 80% of a footprint of the chip.

3. The chip of claim 1 wherein the network of chambers and channels are produced in relief on at least a first side of a first film having a nominal thickness between 20 $\mu$m and 5 mm, and the chip comprises a covering film that covers the first side to enclose the chambers and channels, away from ports of the chip.

4. The chip of claim 1 wherein $d_{pc}$ is nominally maintained despite a pressure relative to ambient by an array of supporting microstructures.

5. The chip of claim 4 wherein the nozzle is located at an entry of the first path to the tc.

6. The chip of claim 1 wherein the entry of the first path to the tc branches to further provide one or more additional instances of the nozzle.

7. The chip of claim 1 wherein the opening between tc and pc is wider than long.

8. The chip of claim 1 wherein a floor of the opening comprises a ramp with a depth varying from $d_{tc}$ to $d_{pc}$.

9. The chip of claim 8 wherein the ramp has a slope of 30° to 75°.

10. The chip of claim 1 comprising a stack of two or more films, at least one of the films having a relief structure defining the network, wherein: each film has a nominal thickness between 20 $\mu$m and 3 mm; each film is composed of a cured or set polymeric compound other than a siloxane; the chip has a thickness of 0.1 to 12 mm; the chip has planar extents of 3 to 25 cm; or the chip has at least 2 ports.

11. The chip of claim 1 wherein the first or second path comprises a metering chamber with an overflow chamber, for volume-controlled delivery.

12. The chip of claim 10 loaded with one or more of: a sample-ready reaction mix, in dried or liquid form in a first chamber within the first path; a sample in dried or liquid form, in a second chamber within the first path; a buffer, solvent, or liquid for dissolving, or suspending the sample or reaction mix within the first path; a dispersion medium adapted to support IRCs loaded within the tc, pc, or rc.

13. The chip of claim 12 further comprising a low density medium chamber coupled to the tc by a third path that meets the tc at an axis-proximal end of the tc, the low density medium chamber loaded with a liquid having a density lower than that of the sample, the buffer, solvent or liquid, and dispersion medium.

14. The chip of claim 1 encased in a cartridge, the cartridge having a rigid structure for ease of manipulation and registration, while providing access to ports of the chip, and avoiding occlusion of vents of the chip.

15. A kit comprising the chip of claim 1 and a chip controller, mounted, or for mounting to, the centrifuge, for rotation of both the chip and controller, the chip controller comprising an off-chip flow control device for selectively displacing fluid in the pc into the rc.

16. The kit of claim 15 wherein the flow control device comprises a pressurized fluid supply line for coupling to a port of the chip.

17. The kit of claim 15 wherein the chip controller, or a cartridge of the kit for encasing and rigidifying the chip, comprises a chip holding surface dimensioned to support the chip on one side thereof, the chip holding surface comprising an energy device for selectively exposing the treatment chamber of the chip to an energy field.

18. The kit of claim 17 wherein the energy field is a thermal energy source or sink, an ultrasonic transducer, or an electromagnetic field generator, in contact with chip adjacent the treatment chamber.

19. The kit of claim 15 further comprising a lighting and imaging system for imaging the pc, during centrifugation, or when the chip is at rest.

20. The kit of claim 15 assembled to form a centrifugal microfluidic system.

21. A method for co-treating emulsion-divided independent reaction volumes (IRVs) and presenting them in a monolayer, the method comprising:

providing the IRVs in the tc of the centrifugal microfluidic chip according to claim 1, by delivering a sample via the first path to form the IRVs;

applying an energy treatment to the IRVs within the tc, by activating an energy device mounted with the chip on a centrifuge while the chip is centrifuged; and operating a flow control device to displace the IRVs from the tc to the to arrange the IRVs in a substantial monolayer, where the flow control device applies a pressure difference of less than 15 kPa.

* * * * *